(12) United States Patent
Igarashi

(10) Patent No.: US 11,883,569 B2
(45) Date of Patent: Jan. 30, 2024

(54) BIOLOGICAL COMPONENT COLLECTION CASSETTE, KIT, OR SYSTEM, AND METHOD OF MANUFACTURE

(71) Applicant: TERUMO KABUSHIKI KAISHA, Tokyo (JP)

(72) Inventor: Masatsugu Igarashi, Shizuoka (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 795 days.

(21) Appl. No.: 16/638,712

(22) PCT Filed: Aug. 9, 2018

(86) PCT No.: PCT/JP2018/029991
§ 371 (c)(1),
(2) Date: Feb. 12, 2020

(87) PCT Pub. No.: WO2019/035415
PCT Pub. Date: Feb. 21, 2019

(65) Prior Publication Data
US 2020/0345906 A1    Nov. 5, 2020

(30) Foreign Application Priority Data

Aug. 14, 2017    (JP) ................. 2017-156560

(51) Int. Cl.
*A61M 1/02*    (2006.01)
*A61M 1/34*    (2006.01)
(Continued)

(52) U.S. Cl.
CPC ........ *A61M 1/0209* (2013.01); *A61M 1/3496* (2013.01); *A61M 1/3672* (2013.01);
(Continued)

(58) Field of Classification Search
CPC .............. A61M 1/0209; A61M 1/3496; A61M 1/3672; A61M 1/3693; A61M 2205/3306;
(Continued)

(56) References Cited

U.S. PATENT DOCUMENTS 4,304,670 A * 12/1981 Watanabe .............. B01D 29/58
D24/162
4,810,451 A    3/1989 Ermert et al.
(Continued)

FOREIGN PATENT DOCUMENTS

EP    1398018    8/2003
JP    H04-37436    3/1992
(Continued)

OTHER PUBLICATIONS

Official Action (with English translation) for Japan Patent Application No. 2019-565036, dated Mar. 1, 2022, 10 pages.
(Continued)

*Primary Examiner* — Craig J Price
*Assistant Examiner* — Andrew J Rost
(74) *Attorney, Agent, or Firm* — Sheridan Ross P.C.

(57) ABSTRACT

A blood component collection cassette has a flow path in the interior thereof through which blood flows, and a cassette main body composed of a resin that possesses flexibility. The cassette main body includes a first constituent part in which a plurality of concavities and convexities are formed. Furthermore, a resin sheet includes a second constituent part, which is provided on one portion of an outer surface of
(Continued)

the flow path wall portion that constitutes the flow path, and in which the plurality of concavities and convexities do not exist.

20 Claims, 8 Drawing Sheets

(51) Int. Cl.
*A61M 1/36* (2006.01)
*B04B 5/04* (2006.01)
*B04B 13/00* (2006.01)

(52) U.S. Cl.
CPC ...... *A61M 1/3693* (2013.01); *A61M 1/36222* (2022.05); *A61M 1/362261* (2022.05); *A61M 1/362264* (2022.05); *A61M 1/362266* (2022.05); *B04B 5/0442* (2013.01); *A61M 2205/3306* (2013.01); *A61M 2205/3375* (2013.01); *A61M 2205/7545* (2013.01); *A61M 2207/00* (2013.01); *B04B 2013/006* (2013.01)

(58) Field of Classification Search
CPC .. A61M 2205/3375; A61M 2205/7545; A61M 2207/00; A61M 1/36222; A61M 1/362266; A61M 1/362264; A61M 1/362261; B04B 5/0442; B04B 2013/006
See application file for complete search history.

(56) References Cited

U.S. PATENT DOCUMENTS

| | | | | |
|---|---|---|---|---|
| 6,270,673 | B1* | 8/2001 | Belt | A61M 1/3451 |
| | | | | 210/646 |
| 6,481,980 | B1* | 11/2002 | Vandlik | F04B 49/065 |
| | | | | 417/313 |
| 6,817,984 | B2* | 11/2004 | Robinson | A61M 1/342 |
| | | | | 210/252 |
| 8,454,553 | B2 | 6/2013 | Fontanazzi et al. | |
| 2007/0278155 | A1* | 12/2007 | Lo | A61M 1/1639 |
| | | | | 210/646 |
| 2009/0163857 | A1 | 6/2009 | Haddad et al. | |
| 2013/0078625 | A1 | 3/2013 | Holmes et al. | |
| 2017/0213012 | A1 | 7/2017 | O'Scolai et al. | |

FOREIGN PATENT DOCUMENTS

| | | |
|---|---|---|
| JP | 2008-086353 | 4/2008 |
| JP | 2013-514863 | 5/2013 |
| WO | 2006091426 A2 | 8/2006 |

OTHER PUBLICATIONS

International Search Report and Written Opinion, PCT/JP2018/029991, dated Feb. 25, 2019, 16 pages.

Official Action for Europe Patent Application No. 18759766.1, dated Jun. 6, 2023, 4 pages.

* cited by examiner

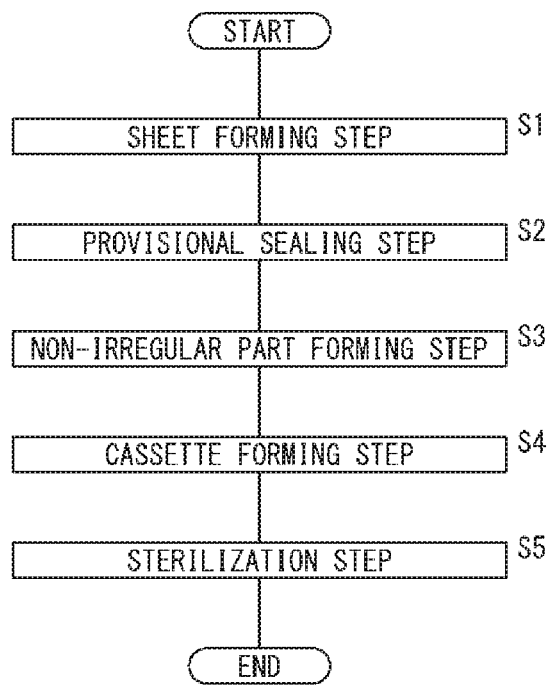

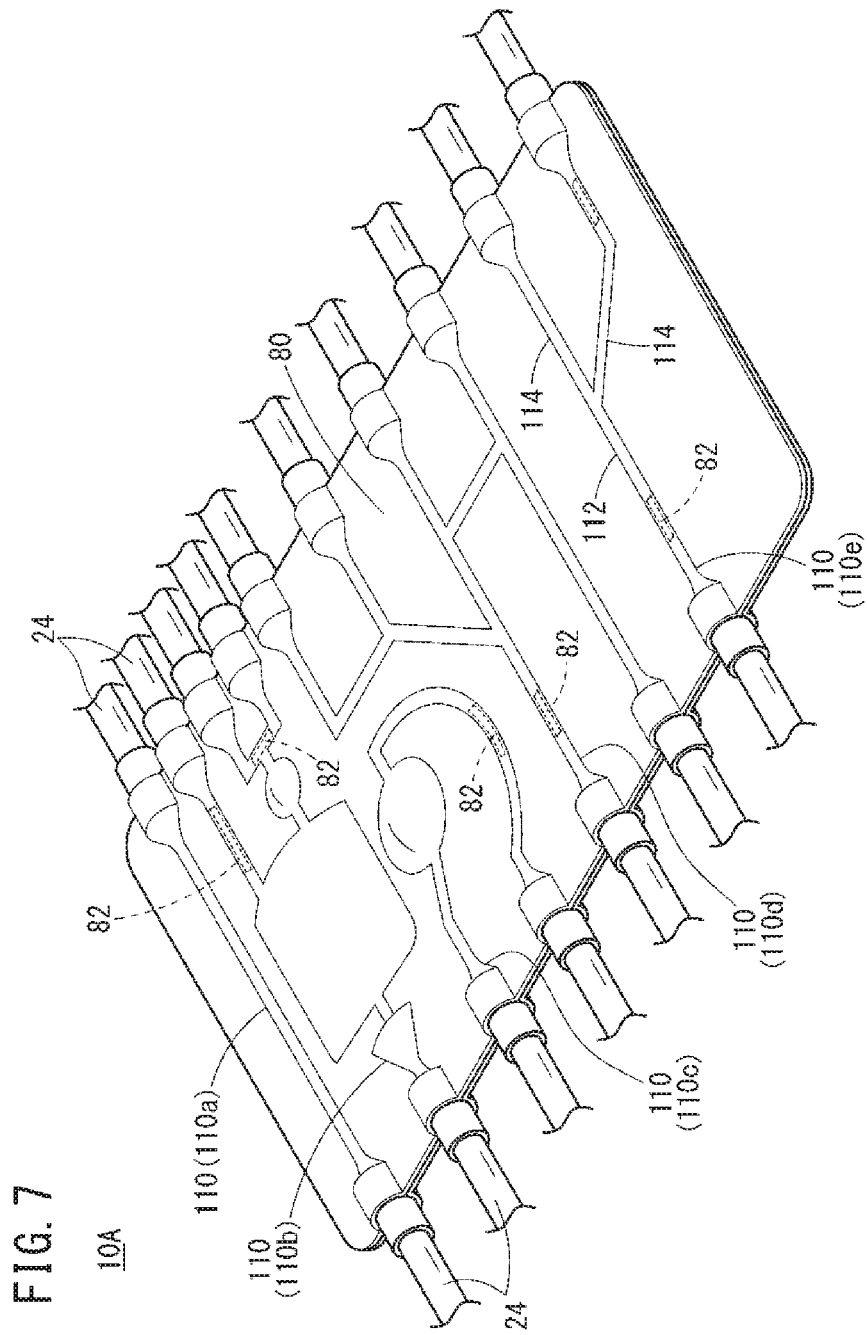

BIOLOGICAL COMPONENT COLLECTION CASSETTE, KIT, OR SYSTEM, AND METHOD OF MANUFACTURE

TECHNICAL FIELD

The present invention relates to a biological component collection cassette, a biological component collection kit, a biological component collection system, and a method of manufacturing a biological component collection cassette.

BACKGROUND ART

Conventionally, in collection of blood components, as disclosed in Japanese Patent Publication No. 2013-514863, a blood component collection cassette having a blood circuit and tubes are set in a blood component separation device, and by performing opening and closing of internal flow paths and driving of a pump, flowing or stopping of flow of blood, switching of flow paths, and the like, are carried out. Examples of the flow paths provided in the blood component collection cassette include a line for introducing blood from a blood donor, and a line for transferring blood components into bags, and the like.

Further, the blood component separation device implements an appropriate control by detecting with a detection unit the state of the blood that flows through the flow paths of the set blood collection kit (blood component collection cassette, tubes).

SUMMARY OF INVENTION

It is desirable for this type of blood component collection cassette (biological component collection cassette) to possess flexibility, together with having a plurality of concavities and convexities formed on an outer surface thereof. As long as the blood collection cassette possesses flexibility, manufacturing can be simplified and costs can be reduced, while in addition, the pressure inside the flow paths can be monitored, and desired flow paths can easily be opened and closed by clamping. Further, the plurality of concavities and convexities are capable of preventing the blood component collection cassette from becoming adhered to a surrounding resin material, and can facilitate taking out and setting of the blood component collection cassette in the blood component separation device.

However, when the plurality of concavities and convexities are formed on outer surfaces of walls constituting the flow paths of the blood component collection cassette, it becomes difficult for the blood component separation device to carry out detection with respect to the cassette by the detection unit. This is because measurement waves (ultrasonic waves or light), which are output from the detection unit, are reflected irregularly or diffusely by impinging on the plurality of concavities and convexities, and further, the plurality of concavities and convexities increases opacity.

The present invention has been devised taking into consideration the aforementioned problem, and has the object of providing a biological component collection cassette, a biological component collection kit, a biological component collection system, and a method of manufacturing a biological component collection cassette, which, with a simple configuration, enables detection of the state of a fluid flowing through a flow path.

In order to achieve the aforementioned object, the present invention is characterized by a biological component collection cassette having a flow path in the interior thereof through which a liquid containing at least one biological component flows, comprising a cassette main body composed of a resin that possesses flexibility, wherein the cassette main body includes a first constituent part constituted from an outer surface having a plurality of concavities and convexities, and a second constituent part constituted from an outer surface on which the plurality of concavities and convexities do not exist, and the second constituent part is provided on at least a part of a flow path wall portion that constitutes the flow path.

In accordance with the above-described invention, the biological component collection cassette is of a simple configuration in which the second constituent part in which the plurality of concavities and convexities do not exist is included in at least a part of the flow path wall portion, and the state of the liquid inside the flow path can be detected. More specifically, since the second constituent part is capable of suitably transmitting the measurement waves of the detection unit of the biological component separation device, it is possible to accurately detect the state of the liquid that flows through the flow path. On the other hand, adhering of the biological component collection cassette to a resin material is prevented by the first constituent part, and therefore taking out of the biological component collection cassette from a storage location is simplified. Accordingly, the blood component collection cassette can be easily set in the blood component separation device, and usability thereof is further improved.

Further, in order to achieve the aforementioned object, the present invention is characterized by a biological component collection cassette having a flow path in the interior thereof through which a liquid containing at least one biological component flows, comprising a cassette main body composed of a resin that possesses flexibility, wherein the cassette main body includes a first constituent part having a low transmittance, and a second constituent part having a transmittance higher than that of the first constituent part, and the second constituent part is provided on at least a part of a flow path wall portion that constitutes the flow path.

As described above, the biological component collection cassette is of a configuration in which the second constituent part having a transmittance higher than that of the first constituent part is included in at least a part of the flow path wall portion, and with this configuration as well, the state of the liquid inside the flow path can be detected accurately.

In addition to the above-described configuration, the first constituent part may be formed by embossing.

The first constituent part is formed by embossing, whereby the first constituent part includes a plurality of minute concavities and convexities, and the transmittance thereof is sufficiently low, and thus, adhering of the cassette main body to a resin material or the like can be prevented.

The second constituent part preferably is formed with a length that is 10% or less than a total length of the flow path.

By forming the second constituent part with a length that is 10% or less than the total length of the flow path, the majority of the flow path wall portion, which protrudes from a planar part of the cassette main body, makes up the first constituent part, and it is possible to significantly suppress the biological component collection cassette from adhering to a resin material.

Furthermore, the first constituent part may be formed with an area which is greater than or equal to 80% of the area of the outer surface of the cassette main body.

The biological component collection cassette includes the first constituent part on 80% or more of the area of the outer surface of the cassette main body, whereby it is possible to more reliably prevent the outer surface of the cassette main body from adhering to a resin material.

Still further, the second constituent part may be disposed on both surfaces of the cassette main body.

By forming the second constituent part on both surfaces of the cassette main body, the biological component collection cassette can apply the detection unit, which carries out detection by transmission of measurement waves, and it is possible to further enhance general versatility.

In addition, the flow path may include a plurality of branching paths, and a trunk path that communicates with the plurality of branching paths, and the second constituent part may be provided in the trunk path.

By including the second constituent part in the trunk path, the biological component collection cassette is capable of detecting in a comprehensive manner the state of the fluid that flows through the trunk path.

In this instance, the resin that constitutes the cassette main body preferably is made up from any one of a vinyl chloride resin, a polyolefin resin, and a polyurethane resin.

By the biological component collection cassette being made up from any one of a vinyl chloride resin, a polyolefin resin, and a polyurethane resin, it is possible to easily form the first constituent part and the second constituent part on the cassette main body. Thus, the manufacturing cost of the biological component collection cassette can be significantly reduced.

Further, in order to achieve the aforementioned object, the present invention is characterized by a biological component collection kit comprising a tube, and a biological component collection cassette communicating with the tube, and having a flow path in the interior thereof through which a liquid containing at least one biological component flows, wherein the biological component collection cassette comprises a cassette main body composed of a resin that possesses flexibility, the cassette main body includes a first constituent part constituted from an outer surface having a plurality of concavities and convexities, and a second constituent part constituted from an outer surface on which the plurality of concavities and convexities do not exist, and the second constituent part is provided on at least a part of a flow path wall portion that constitutes the flow path.

Further, in order to achieve the aforementioned object, the present invention is characterized by a biological component collection kit comprising a tube, and a biological component collection cassette communicating with the tube, and having a flow path in the interior thereof through which a liquid containing at least one biological component flows, wherein the biological component collection cassette comprises a cassette main body composed of a resin that possesses flexibility, the cassette main body includes a first constituent part having a low transmittance, and a second constituent part having a transmittance higher than that of the first constituent part, and the second constituent part is provided on at least a part of a flow path wall portion that constitutes the flow path.

Further, in order to achieve the aforementioned object, the present invention is characterized by a biological component collection system comprising a biological component collection kit including a tube, and a biological component collection cassette communicating with the tube, and having a flow path in the interior thereof through which a liquid containing at least one biological component flows, a biological component separation device to which the biological component collection kit is attached, and through which the biological component contained within the liquid is allowed to flow, wherein the biological component collection cassette comprises a cassette main body composed of a resin that possesses flexibility, the cassette main body includes a first constituent part constituted from an outer surface having a plurality of concavities and convexities, and a second constituent part constituted from an outer surface on which the plurality of concavities and convexities do not exist, and the second constituent part is provided on at least a part of a flow path wall portion that constitutes the flow path, the biological component separation device includes a cassette mounting unit in which the biological component collection cassette is mounted, and the cassette mounting unit includes a detection unit adapted to detect a state of the liquid at a position facing toward the second constituent part.

Further, in order to achieve the aforementioned object, the present invention is characterized by a biological component collection system comprising a biological component collection kit including a tube, and a biological component collection cassette communicating with the tube, and having a flow path in the interior thereof through which a liquid containing at least one biological component flows, a biological component separation device to which the biological component collection kit is attached, and through which the biological component contained within the liquid is allowed to flow, wherein the biological component collection cassette comprises a cassette main body composed of a resin that possesses flexibility, the cassette main body includes a first constituent part having a low transmittance, and a second constituent part having a transmittance higher than that of the first constituent part, and the second constituent part is provided on at least a part of a flow path wall portion that constitutes the flow path, the biological component separation device includes a cassette mounting unit in which the biological component collection cassette is mounted, and the cassette mounting unit includes a detection unit adapted to detect a state of the liquid at a position facing toward the second constituent part.

Further, in order to achieve the aforementioned object, the present invention is characterized by a method of manufacturing a biological component collection cassette having a flow path in the interior thereof through which a liquid containing at least one biological component flows, comprising a sheet supplying step of supplying a resin sheet having a first constituent part constituted from an outer surface having a plurality of concavities and convexities, a non-irregular part forming step of forming a second constituent part on which the plurality of concavities and convexities are eliminated from a predetermined position of the resin sheet, by applying heat to the predetermined position of the resin sheet which is supplied by the sheet supplying step, and a cassette forming step of forming the biological component collection cassette, by after the non-irregular part forming step, sealing the resin sheet while securing the flow path therein.

According to the present invention, in the biological component collection cassette, the biological component collection kit, the biological component collection system, and the method of manufacturing a biological component collection cassette, with a simple configuration, it is possible to detect the state of a fluid flowing through a flow path.

BRIEF DESCRIPTION OF DRAWINGS

FIG. 5 is a flowchart showing a method of manufacturing the blood component collection cassette;

FIG. 7 is a perspective view of a blood component collection cassette according to a modification;

DESCRIPTION OF EMBODIMENTS

Preferred embodiments of the present invention will be presented and described in detail below with reference to the accompanying drawings.

Figure 1:
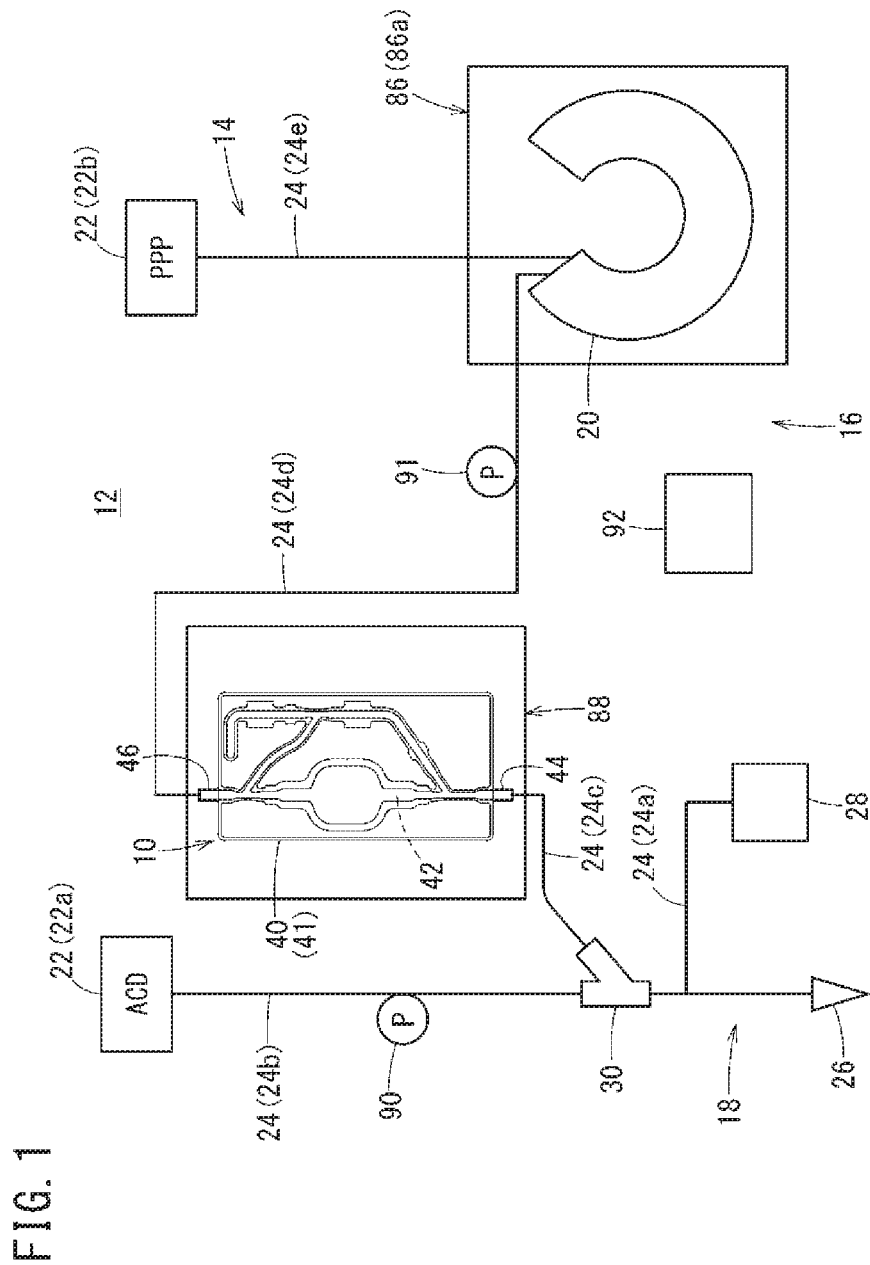
FIG. 1 is a schematic diagram of a blood component collection system according to an embodiment of the present invention.

As shown in FIG. 1, a blood component collection cassette 10 according to one embodiment of the present invention is configured as a biological component collection cassette equipped with a flow path in the interior thereof through which blood (a liquid) containing a blood component (at least one biological component) flows. Hereinafter, in order to facilitate description thereof, the blood component collection cassette 10 will be referred to simply as a cassette 10. In the present specification, the term "blood" is an expression including whole blood, as well as individual blood components, such as plasma, platelets, erythrocytes and the like. The cassette 10 is disposed in one location of a blood collection kit 14 (biological component collection kit) of a blood component collection system 12 (biological component collection system), and allows blood to flow through an internal flow path thereof at a time that blood collection from a blood donor is carried out.

The blood component collection system 12 comprises the aforementioned blood collection kit 14, and a centrifugal separation device 16 (blood component separation device) that applies a centrifugal force to the blood collection kit 14. The blood component collection system 12 is constituted as a blood apheresis system, in which blood (whole blood) is continuously extracted from a blood donor and the blood is centrifugally separated outside the body by the centrifugal separation device 16, whereby a specific blood component (in the present embodiment, plasma [platelet poor plasma: PPP]) is collected, and the remaining blood components are returned to the blood donor.

The blood collection kit 14 includes a blood circuit through which the blood components flow and are stored, and is discarded every time that it is used in order to prevent contamination and ensure sanitation. For example, in addition to the cassette 10, the blood collection kit 14 is equipped with a blood collection and blood returning unit 18, a blood treatment unit 20, a plurality of bags 22, and the like. The cassette 10 is connected to each of these respective elements via a plurality of tubes 24. The plurality of bags 22 include an ACD solution bag 22a containing an ACD solution which is an anticoagulant, and a PPP bag 22b for storing the plasma (platelet poor plasma).

The blood collection and blood returning unit 18 includes a blood collection needle 26 which is punctured and left indwelling in a donor, and an initial flow blood collecting bag 28 in which an initial blood flow is stored at a time of blood donation. The blood collection needle 26 and the initial blood collecting bag 28 are connected to a tube connector 30 via a tube 24a that merges therewith in an intervening location. Further, the ACD solution bag 22a is also connected to the tube connector 30 via an ACD solution transfer tube 24b.

The cassette 10 is connected to the blood collecting and blood returning unit 18 (tube connector 30) via a donor side tube 24c, and is also connected to the blood treatment unit 20 via a treatment unit side tube 24d. The cassette 10 is mounted in a cassette mounting unit 88 of the centrifugal separation device 16 during usage thereof, whereby detection of the state of the fluid flowing through the interior of the cassette 10 under operation of the centrifugal separation device 16, and switching of the flow of the fluid and the like are carried out.

The blood treatment unit 20 is attached to a centrifuge unit 86 (rotor 86a) of the centrifugal separation device 16, and centrifugally separates the whole blood that is extracted from the blood donor into a plurality of blood components. For example, the blood treatment unit 20 is configured in the form of a container which is capable of performing inflow, flow through, and outflow of the blood. Further, the PPP bag 22b is connected to the blood treatment unit 20 via a PPP transfer tube 24e.

Figure 2:
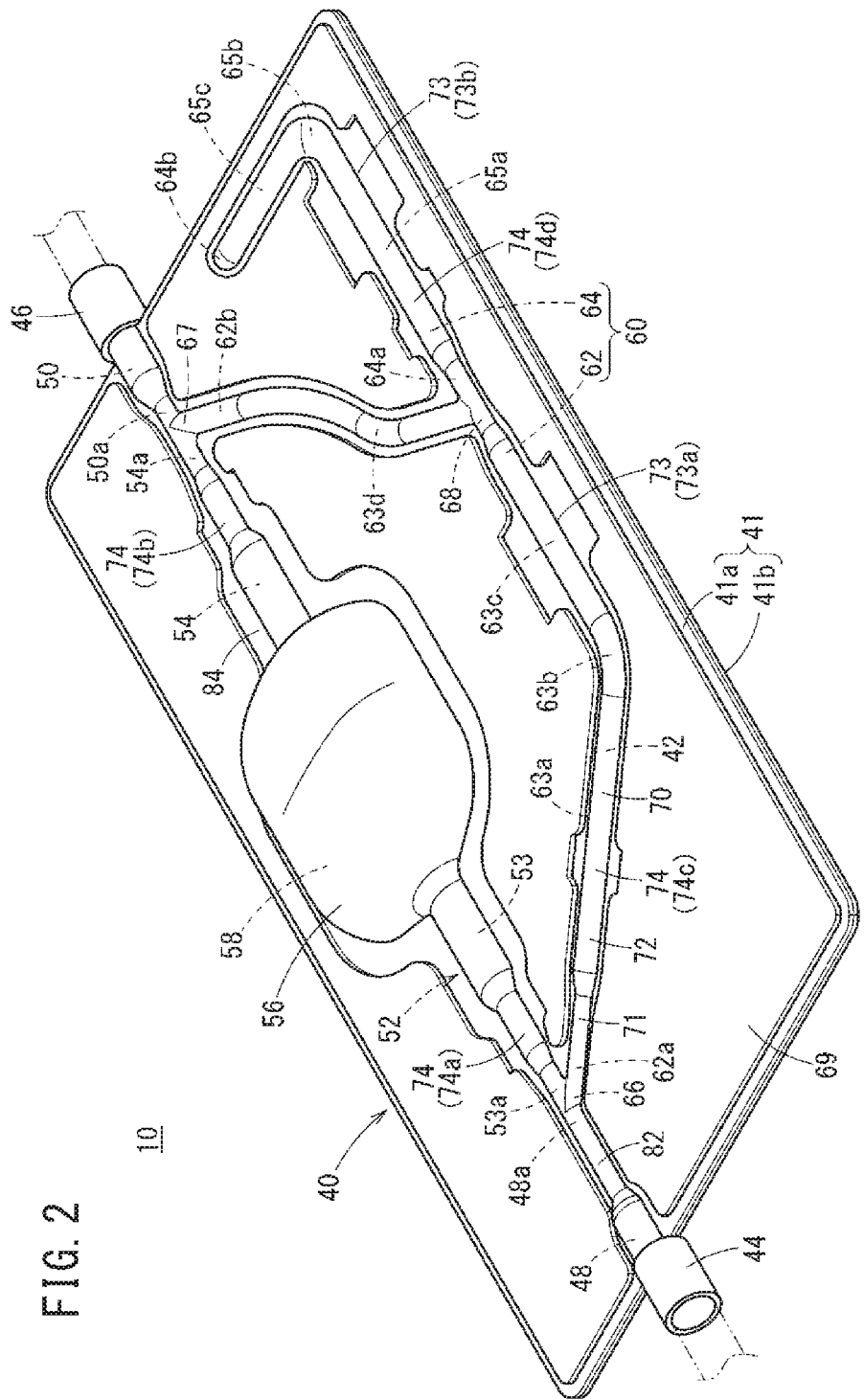
FIG. 2 is a perspective view of a blood component collection cassette.

As shown in FIG. 2, the cassette 10 of the blood collection kit 14 is equipped with a cassette main body 40 provided with a flow path 42 in the interior thereof through which a liquid flows, a first port 44 that communicates with the flow path 42 and a flow path (not shown) of the donor side tube 24c, and a second port 46 that communicates with the flow path 42 and a flow path (not shown) of the treatment unit side tube 24d. The cassette main body 40 is formed in a rectangular shape as viewed in plan. The cassette main body 40 is configured as resin sheets 41 that possess flexibility, by overlapping a first sheet 41a and a second sheet 41b made of a resin material in the thickness direction and joining them together.

The resin that constitutes the cassette main body 40 (the resin sheets 41) is not particularly limited, insofar as it possesses flexibility which is capable of being deformed by pressure of the blood, and as suitable examples thereof, there may be cited vinyl chloride resins, polyolefin resins, polyurethane resins, or the like. In the present embodiment, a vinyl chloride resin is applied. On the other hand, the first and second ports 44, 46 preferably are made of a material that is harder than the material of the cassette main body 40, whereby the donor side tube 24c and the treatment unit side tube 24d can be firmly connected to the cassette main body 40.

The flow path 42 that is formed in the cassette main body 40 includes a first trunk path 48 connected to the first port 44 and extending linearly along the first port 44, and a second trunk path 50 connected to the second port 46 and extending linearly along the second port 46. Further, the flow path 42 extends linearly between the first and second trunk paths 48, 50, and includes a filter line 52 in which a filter member 58 is provided midway therein. Stated otherwise, the first trunk path 48, the filter line 52, and the second trunk path 50 extend linearly in sequential order from the first port 44 to the second port 46.

The filter line 52 includes linearly extending extended portions 53, 54, and a filter accommodating unit 56, which is wider than the extended portions 53, 54, and in which the filter member 58 is accommodated. The filter member 58 removes agglutinated substances (clotted blood) from among the blood components that flow into the filter accommodating unit 56.

Furthermore, the flow path 42 includes a bypass line 60 bypassing the filter line 52. The bypass line 60 includes a first line 62 through which blood flows during operation of the centrifugal separation device 16, and a second line 64 which branches off from the first line 62, and through which blood does not flow during operation of the centrifugal separation device 16.

An end 48a of the first trunk path 48 on an opposite side from the first port 44, one end 53a of the filter line 52, and one end 62a of the first line 62 are mutually connected by a first coupling member 66. An end 50a of the second trunk path 50 on an opposite side from the second port 46, another end 54a of the filter line 52, and another end 62b of the first line 62 are mutually connected by a second coupling member 67. On the other hand, in the second line 64, one end 64a is connected to a third coupling member 68 disposed in a midway position of the first line 62, and another end 64b on the opposite side thereof is closed.

An extended portion 63a, which extends from the one end 62a side of the first line 62, is inclined obliquely with respect to the direction in which the first trunk path 48 and the filter line 52 extend. An extended portion 63c, which is bent at an intermediate curved portion 63b and extends from the extended portion 63a to the third coupling member 68, extends in parallel with the filter line 52. An extended portion 63d on the side of the other end 62b, and which extends from the third coupling member 68 to the second coupling member 67 of the first line 62, meanders moderately and is inclined obliquely with respect to the direction in which the second trunk path 50 and the filter line 52 extend, and is joined to the second trunk path 50.

The second line 64 includes an extended portion 65a which extends linearly from the third coupling member 68 to a curved portion 65b, along the direction in which the extended portion 63c of the first line 62 extends. In addition, an extended portion 65c, which extends from the curved portion 65b to the other end 64b, extends in a direction perpendicular to the direction in which the extended portion 65a extends.

Further, even when a positive pressure is not acting inside the flow path 42, the material (flow path wall portion 70) of the first and second sheets 41a, 41b that make up the flow path 42 bulges in a convex shape in the thickness direction of the resin sheets 41 with respect to the planar part 69 that surrounds the flow path 42. Stated otherwise, both surfaces of the first and second sheets 41a, 41b bulge outwardly due to the flow path wall portion 70. Accordingly, the flow path 42 is opened in a natural state, and when pressed by an external force, the flow path 42 can be elastically deformed in a direction to close the flow path 42 at pressed locations thereof. Moreover, the planar part 69 is formed in a flat shape by the material of the first and second sheets 41a, 41b where the flow path 42 is not formed.

Furthermore, the flow path wall portion 70 is constituted by small-diameter portions 71 having a small flow path cross-sectional area, and large-diameter portions 72 having a flow path cross-sectional area which is larger than that of the small-diameter portions 71. More specifically, the small-diameter portions 71 are provided in the vicinity of each of the first to third coupling members 66 to 68, whereas the large-diameter portions 72 are provided at extended locations away from the first to third coupling members 66 to 68. The ratio of the sizes of the flow path cross-sectional areas of the small-diameter portions 71 and the large-diameter portions 72 is not particularly limited, and for example, the flow path cross-sectional area of the large-diameter portions 72 may be greater than or equal to 1.2 times that of the small-diameter portions 71.

Further, the filter line 52, and the large-diameter portions 72 of each of the first and second lines 62, 64 are formed with the same thickness, and the rigidities thereof are also set to be the same. In addition, in a mounted state in which the cassette 10 is installed in the centrifugal separation device 16, predetermined locations of the large-diameter portions 72 of the first and second lines 62, 64 serve as detected parts 73 (first detected part 73a, second detected part 73b) that are pressed by load detection units 96 (see FIG. 3). Moreover, the detected parts 73 may be formed with a flow path cross-sectional area which is greater than that of the large-diameter portions 72.

Furthermore, on the cassette 10, there are provided a plurality of clamp action members 74 (first to fourth clamp action members 74a to 74d) on which a plurality of clamps 98 (see FIG. 3), which are provided in the centrifugal separation device 16, act. The clamp action members 74 are portions that abut against or are placed at positions facing their corresponding clamps 98 of the centrifugal separation device 16. More specifically, the clamp action members 74 are provided respectively with a large-diameter portion 72 in proximity to the first coupling member 66 of the first line 62, a large-diameter portion 72 in proximity to the third coupling member 68 of the second line 64, and large-diameter portions 72 in proximity to the first and second coupling members 66, 67 of the filter line 52.

Figure 4:
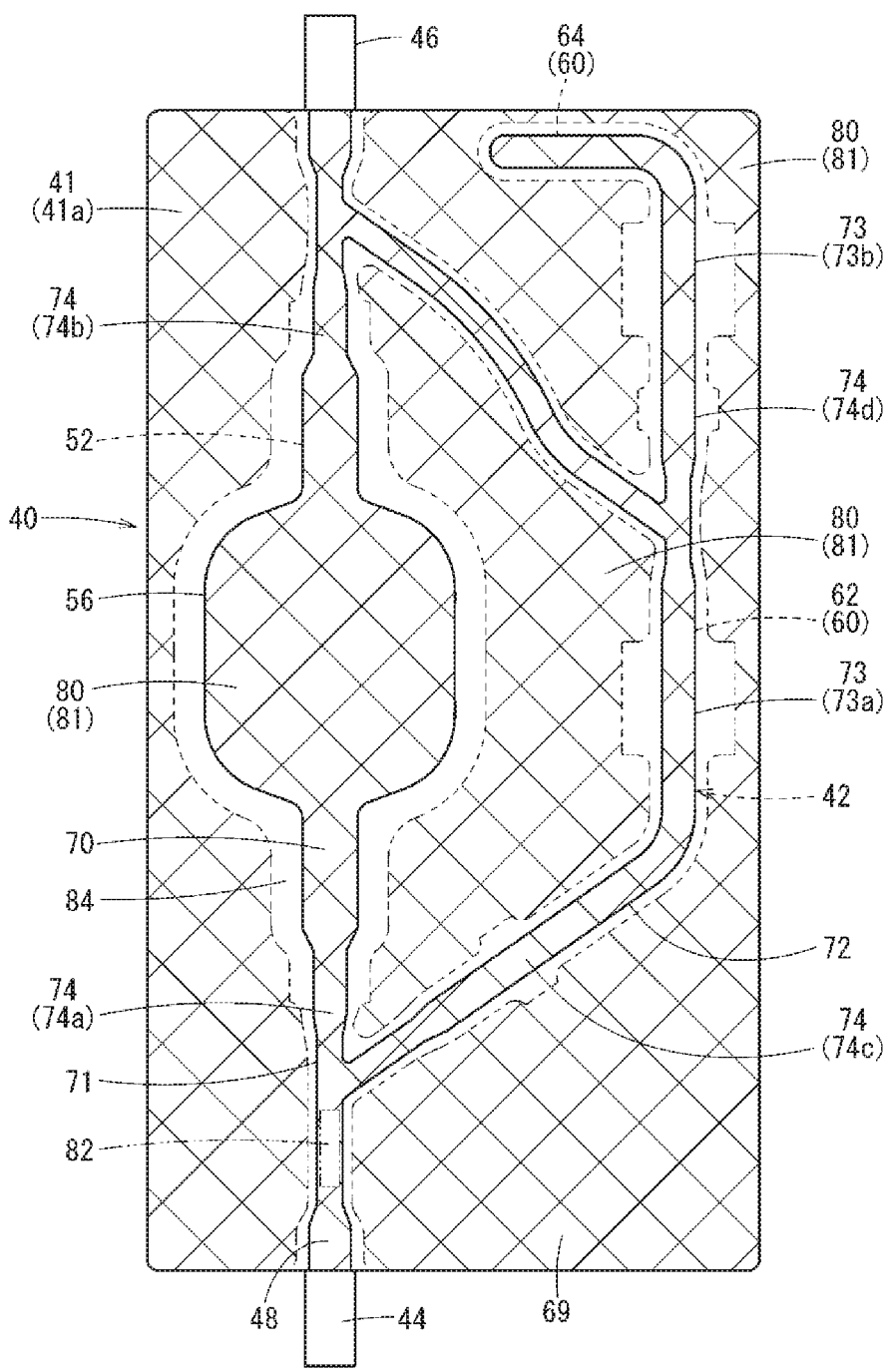
FIG. 4 is a plan view for describing the state of an outer surface of the blood component collection cassette.

Additionally, as shown in FIG. 4, the majority of the cassette 10 (cassette main body 40) according to the present embodiment is made up of the first constituent part 80, which is formed on the outer surface and has a plurality of concavities and convexities 81 therein (in FIG. 4, a state in which the outer surface of the first sheet 41a is viewed in plan is exemplified in a representative manner). The first constituent part 80 makes the outer surface of the resin sheets 41 feel rough to the touch, by providing fine embossments 81a (see FIG. 6) made up of a plurality of concavities and convexities 81 thereon.

For example, it is preferable that the first constituent part 80 be formed over an area that is greater than or equal to 80% of the entire outer surface of the first and second sheets 41a, 41b. By forming the first constituent part 80 to lie within a range of 80% or greater, adhering of a plurality of cassettes 10 to themselves when placed in storage, or adhering thereof to a package made of a resin material is prevented. Further, the first constituent part 80 exhibits an opacity due to the plurality of concavities and convexities 81, and constitutes a low light transmissive portion which makes the flow path 42 difficult to observe from the exterior. The opacity of the first constituent part 80 includes a low transmittance (for example, a transmittance of 50% or less) which, although it can be recognized from the exterior that a liquid is flowing, is of a degree in which the color of blood cannot be recognized sufficiently. Of course, the first constituent part 80 may have a transmittance that makes it impossible to completely distinguish the liquid from the exterior.

The individual embossments 81*a* are formed in convex shapes of, for example, about several hundred micrometers to several mm by an embossing process (refer also to the manufacturing method, to be described later), and the embossments 81*a* are separated mutually from each other by about several hundred micrometers to several mm, and are arranged in a surface direction. Consequently, the first constituent part 80 exhibits a series of concavities and convexities 81 in which the fine embossments 81*a* thereof are arranged in a regular manner. Moreover, the embossments 81*a* may protrude by a short distance from the outer surface, and are formed to have a projecting height, for example, of several tens of micrometers to several micrometers.

Further, the cassette 10 includes the second constituent part 82, which is provided on the outer surface in close proximity to the first coupling member 66 (end 48*a*) of the first trunk path 48. Since the second constituent part 82 is formed by a smooth outer circumferential surface in which the plurality of concavities and convexities 81 do not exist, the transparency thereof is higher than that of the surrounding first constituent part 80. More specifically, the second constituent part 82 has a transparency that is capable of sufficiently transmitting light, and by not having the plurality of concavities and convexities 81, reduces diffuse reflection of sound in the case that sound waves are transmitted thereto. The transparency of the second constituent part 82 includes a high transmittance (for example, a transmittance of greater than or equal to 70%), which enables the color of the blood flowing through the flow path 42 to be sufficiently discriminated. Stated otherwise, the second constituent part 82 is configured as a high transmissive component having a transmittance higher than that of the first constituent part 80. Consequently, the second constituent part 82 significantly reduces detection noise produced by the detection unit 100 (see FIG. 3: detection sensor) of the centrifugal separation device 16.

In a cross-sectional view of the first trunk path 48, the second constituent part 82 is formed on both surfaces (both the first and second sheets 41*a*, 41*b*) of the resin sheets 41. Further, as viewed in cross-section, the second constituent part 82 is formed over the entirety of a portion that protrudes from the planar part 69 of the flow path wall portion 70.

Furthermore, the second constituent part 82 is disposed only on a location where the small-diameter portion 71 of the first trunk path 48 is formed. Therefore, the formation region of the second constituent part 82 is formed to have a length of less than or equal to 10% of the entire length of the flow path 42 (the first trunk path 48, the second trunk path 50, the filter line 52, and the bypass line 60). In this manner, assuming that the length thereof is less than or equal to 10%, the formation region of the second constituent part 82 is negligible in contrast to the region in which the first constituent part 80 is formed, which is provided over the entirety of the cassette 10, and the function of the first constituent part 80 can be adequately exhibited.

Moreover, in the cassette main body 40, heat sealing is carried out at a time of forming the flow path 42 at a position adjacent to the flow path 42 (at locations in contact with the flow path 42 on the planar part 69), whereby a sealed section 84 is formed where the plurality of concavities and convexities 81 are crushed (do not exist). The sealed section 84 is recessed slightly in the thickness direction of the resin sheets 41 with respect to the first constituent part 80. Therefore, when the cassettes 10 are placed in storage or the like, it is difficult for the sealed sections 84 thereof to come into contact with each other, and adhesion therebetween is suppressed.

Returning to FIG. 1, the centrifugal separation device 16 in which the above-described blood collection kit 14 (including the cassette 10) is mounted is a device that is used repeatedly during blood component collection, and is provided, for example, in a medical facility, a blood collection vehicle, or the like. The centrifugal separation device 16 is equipped with the centrifuge unit 86 having the rotor 86*a*, and the cassette mounting unit 88 which is configured to be capable of having the cassette 10 of the blood collection kit 14 mounted therein.

Further, the centrifugal separation device 16 includes an ACD solution transfer pump 90 that acts on the ACD solution transfer tube 24*b*, and a blood collection and blood returning pump 91, which acts on the treatment unit side tube 24*d* that is connected to the cassette 10. The ACD solution transfer pump 90 is a pump that transfers the ACD solution from the ACD solution bag 22*a* to the cassette 10 and the blood treatment unit 20 via the ACD solution transfer tube 24*b*. The blood collection and blood returning pump 91 is a pump that transfers blood from the blood donor to the blood treatment unit 20, and together therewith, transfers blood from the blood treatment unit 20 back to the blood donor. For example, a roller pump or a finger pump or the like can be applied to the ACD solution transfer pump 90 and the blood collection and blood returning pump 91.

The centrifugal separation device 16 further includes a control unit 92 adapted to control the centrifuge unit 86, the cassette mounting unit 88, and the pumps 90, 91. Operations of the aforementioned plurality of clamps 98 are controlled by the control unit 92. Further, during operation of the centrifugal separation device 16, the control unit 92 acquires (calculates) the internal pressure of the blood circuit of the blood collection kit 14, on the basis of the loads detected by the load detection units 96 (see FIG. 3).

Figure 3:
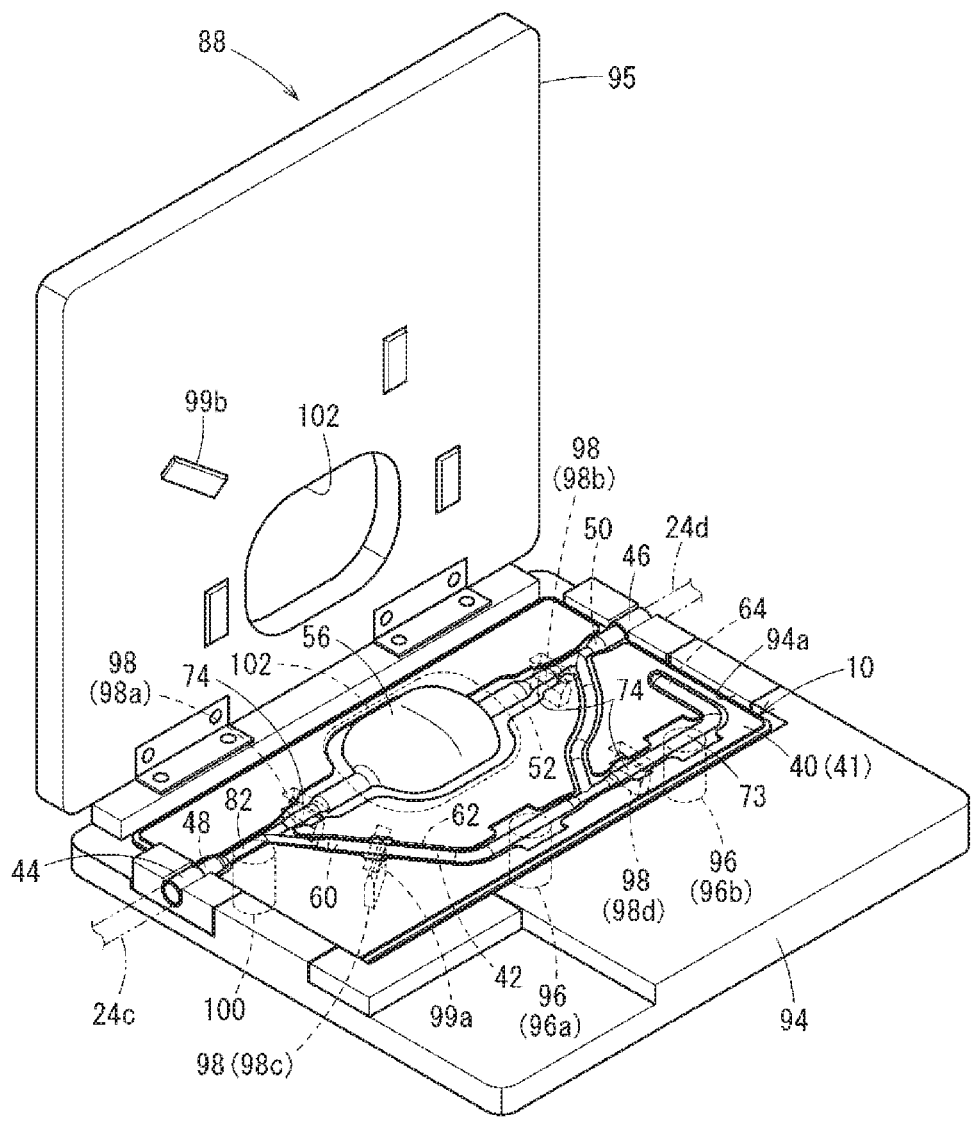
FIG. 3 is a perspective view of a cassette mounting unit in a state with the blood component collection cassette placed therein.

As shown in FIG. 3, the cassette mounting unit 88 includes an attachment base 94 having a cassette mounting groove 94*a* formed therein, and a lid 95 which can be opened and closed and is configured in a manner to cover the attachment base 94 when closed. Further, at predetermined locations of the attachment base 94, there are provided a plurality of load detection units 96 (first load detection unit 96*a*, second load detection unit 96*b*), which are capable of pressing on the detected parts 73 of the cassette 10, a plurality of clamps 98 (first to fourth clamps 98*a* to 98*d*) that enable the clamp action members 74 of the cassette 10 to be opened and closed, and a detection unit 100 adapted to detect a state of the liquid.

When the lid 95 is closed in a state with the cassette 10 being held in the cassette mounting groove 94*a* of the attachment base 94, the cassette 10 is sandwiched between the attachment base 94 and the lid 95. On the attachment base 94 and the lid 95, there are respectively provided openings 102, which are capable of receiving the filter accommodating unit 56 of the cassette 10. The openings 102 retain the cassette 10 appropriately, while also preventing the filter accommodating unit 56 from being crushed.

The load detection units 96 include non-illustrated detection surfaces that are exposed (project out) at the same height from the bottom surface of the cassette mounting groove 94*a* of the attachment base 94. The load detection units 96 are constituted, for example, by load cells.

The plurality of clamps 98 are disposed at positions corresponding to the clamp action members 74 of the cassette 10, and are advanced and retracted in the thickness direction of the resin sheets 41 that are held in the cassette mounting groove 94a, via a plurality of holes 99a that open on the bottom surface of the cassette mounting groove 94a. Further, on the lid 95, projections 99b are provided at positions that face toward the plurality of holes 99a (clamps 98) when the lid 95 is closed, and the respective clamps 98 operate in cooperation with the opposing projections 99b, so as to press on (squash) the respective clamp action members 74.

In a state with the cassette 10 being mounted in the cassette mounting unit 88, at a time that the clamp action members 74 are not being pressed by the clamps 98, the flow path 42 in the interior thereof is opened. When the clamps 98 press on the clamp action members 74, the flow path 42 in the interior of the clamp action members 74 is closed. When the clamps 98 are retracted, due to the elastic restorative force of (the clamp action members 74 of) the cassette main body 40, the clamp action members 74 are restored to their original shape, and the flow path 42 inside the clamp action members 74 is opened.

Further, in a state in which the cassette main body 40 is mounted in the cassette mounting unit 88, the detection unit 100 is disposed at a position facing toward the second constituent part 82. The detection unit 100 outputs measurement waves, which are directed toward the flow path 42 inside the second constituent part 82, and together therewith, includes measurement end portions 101a, 101b (see FIG. 6), which receive transmitted waves or reflected waves, and thereby detect the state of the fluid (blood, medicine, the presence or absence of air (gas), or the like).

Various elements can be adopted as the detection unit 100. For example, an ultrasonic sensor or an optical sensor can be applied thereto. An ultrasonic sensor outputs ultrasonic waves and detects reflected sound therefrom. Owing thereto, the control unit 92 of the centrifugal separation device 16 is capable of determining whether or not air exists within the flow path 42. On the other hand, an optical sensor outputs measurement light of a predetermined wavelength, and detects reflected light or transmitted light therefrom. Owing thereto, the control unit 92 is capable of accurately detecting the state of the blood (whole blood, erythrocytes, etc.) that flows through the first trunk path 48.

Next, with reference to FIG. 5, a method of manufacturing the above-noted cassette 10 will be described. The cassette 10 according to the present embodiment is manufactured by carrying out in sequential order a sheet forming step (sheet supplying step) of forming a series of the resin sheets 41, a provisional sealing step of provisionally sealing the resin sheets 41, a non-irregular part forming step of eliminating the concavities and convexities 81 from the resin sheets 41, and a cassette forming step of forming the cassette 10 so as to have the flow path 42 therein. Furthermore, in manufacturing the cassette 10, a sterilization step of subjecting the cassette 10 to sterilization may be carried out after the cassette forming step.

More specifically, in the sheet forming step, a series of the resin sheets 41 (first and second sheets 41a, 41b) is injection molded from a resin material (vinyl chloride resin) using a non-illustrated injection molding machine. In forming the resin sheets 41, a thickness or the like of the sheets is adjusted through a gap formed between a pair of non-illustrated rollers. In the pair of rollers, a concave and convex shaped mold is formed in advance on an outer circumferential surface of one of the rollers, whereas a smooth roll surface is formed in advance on the outer circumferential surface of the other of the rollers. Accordingly, when the pair of rollers push inwardly on the resin sheets 41 in a thickness direction and feed out the resin sheets 41, embossing is performed thereon by the concave and convex shaped mold. Consequently, the resin sheets 41 are manufactured in a state in which a plurality of the embossments 81a (concavities and convexities 81) are provided on one surface, and a smooth surface is provided on the other surface thereof, and the resin sheets 41 are wound into a roll.

In the provisional sealing step, the series of the resin sheets 41 is fed out from the roll using a non-illustrated joining device, the resin sheets 41 are overlapped in a manner so that the plurality of concavities and convexities 81 are positioned on the outer surface side, provisional sealing thereof is performed, and the sheets 41 are set within a forming range of the cassette main body 40. Also, at the time of provisional sealing, components to be assembled (the filter member 58, port members of the first and second ports 44, 46) are supplied to the joining device, and the components to be assembled also are positioned and provisionally fixed in place.

In addition, in the non-irregular part forming step, a pair of non-illustrated heat sealers are advanced and brought into contact with intended formation positions (predetermined positions) of the second constituent part 82 within the forming range of the provisionally sealed cassette main body 40. Contacting portions of the pair of heat sealers are capable of applying a set quantity of heat to the resin sheets 41. For example, the amount of heat of the contacting portions of the heat sealers preferably ranges from 120° C. to 200° C., and according to the present embodiment, the temperature of the pair of heat sealers is set to 140° C.

Consequently, among the plurality of embossments 81a that are formed over the entire surface of the resin sheet 41, a plurality of the embossments 81a of portions sandwiched between the pair of heat sealers are crushed. Further, since the amount of heat of the heat sealers is not so large as to significantly melt the overlapped resin sheets 41 (the first and second sheets 41a, 41b), fusion of the resin sheets 41 to each other is inhibited. As a result, the first constituent part 80 and the second constituent part 82 are made to exist on the outer surfaces of the resin sheets 41.

In addition, in the cassette forming step, the resin sheets 41 are fusion bonded (primary sealing is performed) so as to produce the flow path 42 between the first sheet 41a and the second sheet 41b, and the cassette 10 equipped with the cassette main body 40 is formed.

For example, the joining device includes upper and lower molds, and applies heat with respect to the resin sheets 41, with the components to be assembled provisionally sealed therein, in the vicinity of the flow path 42 while blow-molding the flow path 42. Consequently, the sealed section 84 is formed, and the flow path 42 is formed inside the sealed section 84. Moreover, although detailed explanation thereof is omitted, at the time of forming the cassette 10 in the joining device, the tubes 24 may be connected, and the blood collection kit 14 may be formed simultaneously together with manufacturing the cassette 10.

Further, in the sterilization step, for example, autoclave sterilization is performed on the obtained cassette 10. The cassette 10 is constituted from a material that is permeable to water vapor, and such water vapor, which is a treatment gas employed in autoclave sterilization, is introduced into the flow path 42 of the cassette 10, whereby sterilization of the cassette 10 can be suitably performed. Moreover, in the sterilization step, EOG sterilization may be performed, or the entirety of the blood circuit including the plurality of bags 22 (ACD solution bag 22a, etc.) may be sterilized.

Next, operations of the cassette 10, the blood component collection system 12, and the blood collection kit 14 according to the present embodiment will be described.

As a preparation for collecting blood components from a blood donor using the blood component collection system 12 shown in FIG. 1, the blood collection kit 14 is mounted in the centrifugal separation device 16. In this instance, by forming the first constituent part 80 on the outer surface, adhering of the cassette 10 to another cassette 10 (or alternatively, a packaging bag accommodating the blood collection kit 14) that is stored in a storage location is prevented. Thus, the blood collection kit 14 can easily be taken out from the storage location.

After the blood collection kit 14 is taken out, the cassette 10 is mounted in the cassette mounting unit 88, and the blood treatment unit 20 is attached to the rotor 86a. In addition, the blood collecting needle 26 pierces and is inserted into the blood donor.

As shown in FIG. 3, when attached to the cassette mounting unit 88, the cassette 10 is mounted in the cassette mounting groove 94a. In addition, by closing the lid 95, the cassette 10 is placed in a state of being held between the lid 95 and the attachment base 94. In this state, the plurality of detected parts 73 of the cassette main body 40 are arranged, respectively, to face the load detection units 96, and the plurality of clamp action members 74 are arranged, respectively, to face the clamps 98. Further, the second constituent part 82 is arranged to face the detection unit 100 of the cassette mounting unit 88.

When operation thereof is initiated by an operation of the user, under an action of the ACD solution transfer pump 90, the centrifugal separation device 16 carries out priming by the ACD solution. The ACD solution is introduced into the flow path 42 inside the cassette 10 from the ACD solution bag 22a and via the ACD solution transfer tube 24b. When arrival of the ACD solution is detected by the detection unit 100 of the cassette mounting unit 88, the centrifugal separation device 16 terminates priming by the ACD solution.

Next, by rotating the rotor 86a, the centrifugal separation device 16 applies a centrifugal force to the blood treatment unit 20 that is attached to the rotor 86a, and further, by operation of the blood collection and blood returning pump 91, blood (whole blood) from the blood donor is extracted and introduced into the blood treatment unit 20. By the centrifugal force that accompanies rotation of the rotor 86a, the blood introduced into the blood treatment unit 20 is separated into red blood cells (concentrated red blood cells), a buffy coat, and plasma (platelet poor plasma).

The plasma that is separated inside the blood treatment unit 20 is introduced into the PPP bag 22b via the PPP transfer tube 24e. After completion of the centrifugal separation process, the remaining blood components (the red blood cells and the buffy coat) are returned to the blood donor (blood returning operation). At this time, blood clumps (clotted blood) contained within the remaining blood components are trapped by the filter member 58 that is provided in the filter line 52 of the cassette 10. Therefore, any risk of clotted blood being returned to the blood donor is reduced. The above-described blood collection operation and blood returning operation are repeated a plurality of times.

Further, the centrifugal separation device 16 individually controls the plurality of clamps 98 during implementation of the above-described priming, blood collection, and blood returning operations, and thereby controls opening and closing of the flow paths of the filter line 52, the first line 62, and the second line 64. Furthermore, by the plurality of load detection units 96, the centrifugal separation device 16 individually detects the detected parts 73 of the first and second lines 62, 64, to thereby measure the internal pressure in the respective sections of the flow path 42, and switch the control content or correct the detected values.

Figure 6A:
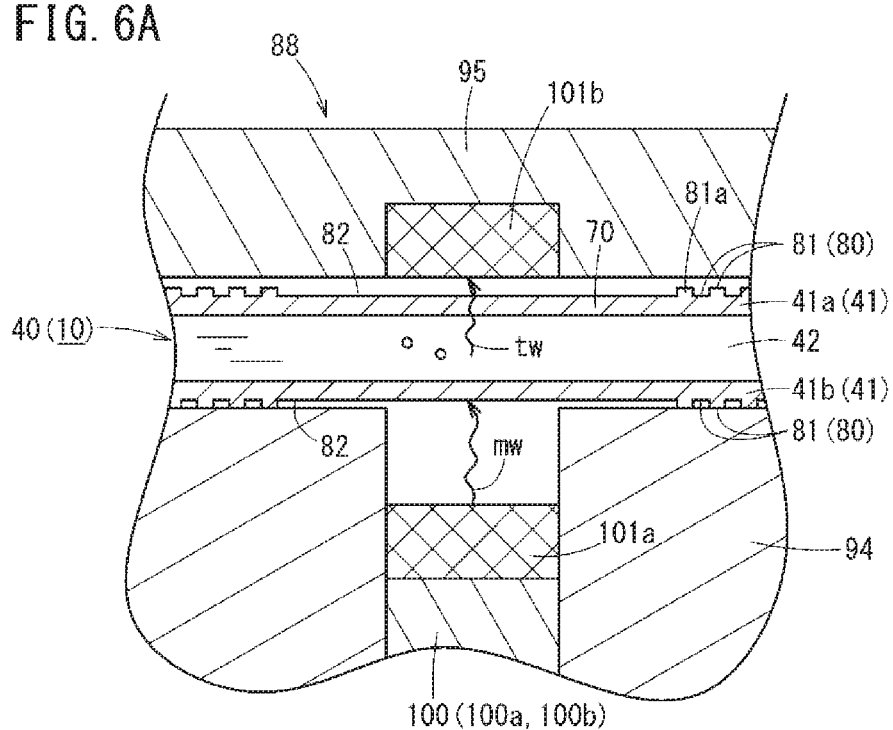
FIG. 6A is a schematic side cross-sectional view for describing an action of a second constituent part of the blood component collection cassette.

In addition, during implementation of the above-described priming, blood collection, and blood returning operations, as shown in FIG. 6A, the blood component collection system 12 detects the state of the blood by the detection unit 100 (ultrasonic sensor 100a). More specifically, the measurement end portion 101a of the ultrasonic sensor 100a outputs ultrasonic waves (measurement waves mw) toward the second constituent part 82 of the cassette 10, and the transmitted waves tw therefrom are detected by the measurement end portion 101b provided in the lid 95. Further, by detecting attenuation or blocking of the transmitted waves tw, the ultrasonic sensor 100a detects the presence or absence of blood (or the ACD solution) or air that flows through the flow path 42 inside the second constituent part 82.

Figure 6B:
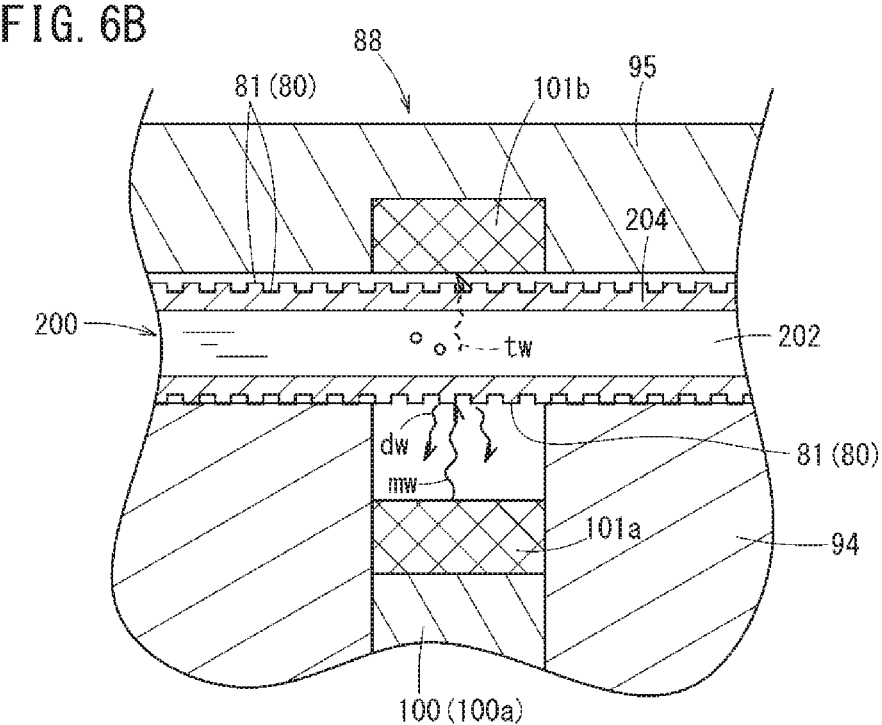
FIG. 6B is a schematic side cross-sectional view for describing an action of a blood component collection cassette according to a comparative example.

In this instance, in the case that the first constituent part 80 (the plurality of concavities and convexities 81) is formed on the outer surface of the flow path wall portion 204 of the flow path 202, as in the cassette 200 according to the comparative example shown in FIG. 6B, the ultrasonic waves that are output from the ultrasonic sensor 100a impinge on the first constituent part 80 and produce diffuse reflections dr. Therefore, attenuation of the ultrasonic waves that arrive at the flow path 202 increases, and the transmitted waves tw also are extremely attenuated. Thus, in the cassette 200, it is difficult to accurately detect the state (presence or absence) of the liquid or gas flowing through the flow path 202.

In contrast thereto, the cassette 10 according to the present embodiment includes the second constituent part 82 at a position facing toward the ultrasonic sensor 100a. Therefore, diffuse reflections dr of the ultrasonic waves are suppressed, and the ultrasonic waves are transmitted through the flow path wall portion 70. Further, attenuation of the transmitted waves tw is also suppressed. Accordingly, the centrifugal separation device 16 can accurately detect the liquid or gas flowing through the flow path 42 of the cassette 10, and it is possible to adequately carry out control of the centrifugal separation.

The detection unit 100 (ultrasonic sensor 100a) may include on the same side (on the side of the cassette mounting unit 88) an output unit and a reception unit that output and receive the measurement waves. In accordance with this feature, the detection unit 100 can be configured to detect the state of the liquid by receiving reflected waves, instead of the transmitted waves tw that pass through the second constituent part 82.

Further, in the case that an optical sensor 100b is applied as the detection unit 100, measurement light (measurement waves mw) emitted from a light emitting unit of the optical sensor 100b impinge on the second constituent part 82. As discussed above, since the second constituent part 82 possesses transparency (the transmittance thereof is high), the measurement light passes easily through the flow path wall portion 70, and is received by a light receiving unit (the measurement end portion 101b), which is provided on a side opposite from the light emitting unit. Accordingly, the centrifugal separation device 16 can accurately detect the color of the liquid that flows through the flow path 42 of the cassette 10 (whole blood during blood collection, erythrocytes when returning the blood, or the ACD solution at a time of priming), and it is possible to adequately carry out control of the centrifugal separation.

As can be appreciated from the above, the cassette 10, the blood component collection system 12, and the blood collection kit 14 according to the present embodiment produce the following effects.

In the cassette 10, by the majority of the outer surface of the resin sheet 41 being constituted by the first constituent part 80, and by including the second constituent part 82 on one portion of the outer surface of the flow path wall portion 70, without losing the function of the first constituent part 80, it is possible to detect the state of the liquid inside the flow path 42. More specifically, adhering of the cassette 10 to a resin material is prevented by the first constituent part 80, and therefore taking out of the cassette 10 from a storage location is simplified. On the other hand, the second constituent part 82 can suitably transmit the measurement waves of the detection unit 100, and can accurately detect the state of the fluid flowing through the flow path 42. Accordingly, the cassette 10, the blood component collection system 12, and the blood collection kit 14 can be easily set in the cassette mounting unit 88 having the detection unit 100, and usability thereof is further enhanced.

Further, in the cassette 10, the length of the second constituent part 82 is less than or equal to 10% of the total length of the flow path 42. Therefore, the first constituent part 80 exists on a portion that occupies 90% or more of the flow path 42, and it is possible to significantly suppress the flow path wall portion 70, which protrudes from the planar part 69 of the resin sheet 41, from adhering to a resin material. Furthermore, in the cassette 10, by including the first constituent part 80 on 80% or more of the area of the outer surface of the resin sheets 41, it is possible to more reliably prevent the outer surface of the resin sheets 41 from adhering to a resin material.

Still further, in the cassette 10, by forming the second constituent part 82 on both surfaces of the resin sheets 41, it is possible to apply the detection unit 100, which performs detection by transmitting the measurement waves in the blood component collection system 12. Stated otherwise, the versatility of the cassette 10 is further enhanced. In addition, by including the second constituent part 82 in the first trunk path 48, the blood component collection cassette 10 is capable of detecting in a comprehensive manner the state of the fluid that flows through the first trunk path 48. Further, assuming that the blood component collection cassette 10 is made up from a vinyl chloride resin, it is possible to easily form the first constituent part 80 and the second constituent part 82 on the resin sheets 41. Thus, the manufacturing cost of the blood component collection cassette 10 can be significantly reduced.

The present invention is not limited to the above-described embodiment, and various modifications can be adopted in accordance with the essence and gist of the present invention. For example, on the cassette main body 40, the second constituent part 82 without the concavities and convexities 81 need not necessarily be formed on both of the first and second sheets 41a, 41b, and the second constituent part 82 may be provided only on one surface side (for example, on the side of the second sheet 41b) that faces toward the detection unit 100.

Further, the second constituent part 82 may be disposed on the detected parts 73 so as to face to the load detection units 96 of the centrifugal separation device 16, and accordingly, it can be expected to increase the detection accuracy of the loads detected by the load detection units 96. Furthermore, the flow path configuration of the cassette 10, and the number and arrangement of the bags 22 provided in the blood collection kit 14 are not limited to the above-described configuration, and may be modified depending on the type of blood components to be collected, the method of use, and the like.

For example, the cassette 10A (blood component collection cassette 10A) according to the modification shown in FIG. 7 includes a plurality of mutually independent flow paths 110, and a configuration can be provided in which the flow paths 110 are connected respectively to tubes 24 via ports of each of the flow paths 110. In this case, predetermined flow paths (in FIG. 7, the flow paths 110b, 110d, 110e) from among the plurality of flow paths 110 may be of a configuration including trunk paths 112, and a plurality of branching paths 114 that branch off from the trunk paths 112.

With such a cassette 10 as well, the first constituent part 80 may be provided on the majority of the outer surface including the flow paths 110, and the second constituent part 82 may be provided on portions of the outer surface of the flow path wall portion 70.

For example, apart from being provided on the trunk paths 112, the second constituent part 82 may be provided in the branching paths 114, or may be provided in coupling members that interconnect the trunk paths 112 and the branching paths 114. Further, the second constituent part 82 may be provided not only on linearly extending portions of the flow paths 110, but also may be provided on curved or bent portions thereof.

Furthermore, two or more of the second constituent parts 82 may be provided in one of the flow paths 110, or one of the second constituent parts 82 may be made to extend over a certain length. For example, the velocity of the fluid inside the flow paths 110 can be calculated by detecting the state of the fluid, by the second constituent part 82 and the detection units 100 (see FIG. 3) provided in upstream and downstream locations thereof. Further, it is also possible to detect the state of the liquid by plural types of detection units 100, such as the ultrasonic sensor 100a and the optical sensor 100b or the like.

Figure 8A:
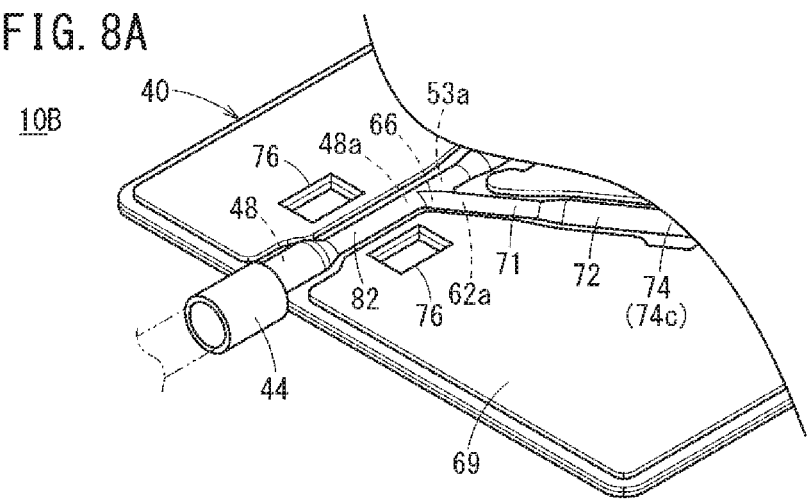
FIG. 8A is a partial perspective view of a blood component collection cassette according to another modification.
Figure 8B:
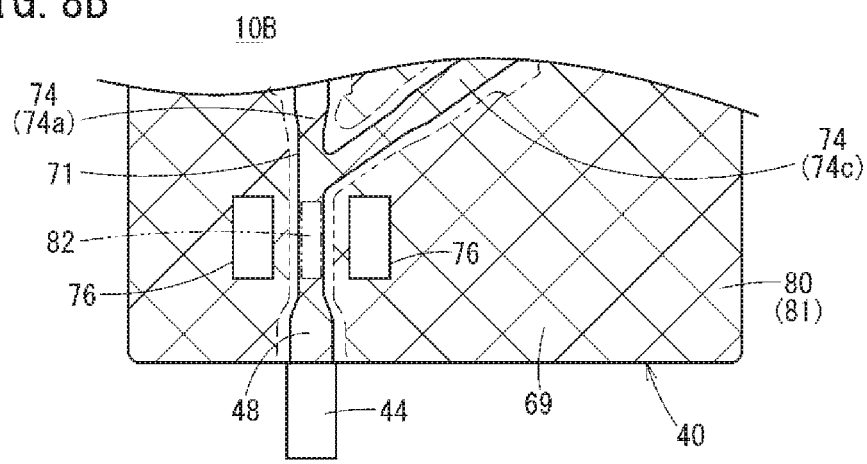
FIG. 8B is a partial plan view of the blood component collection cassette of FIG. 8A.
Figure 8C:
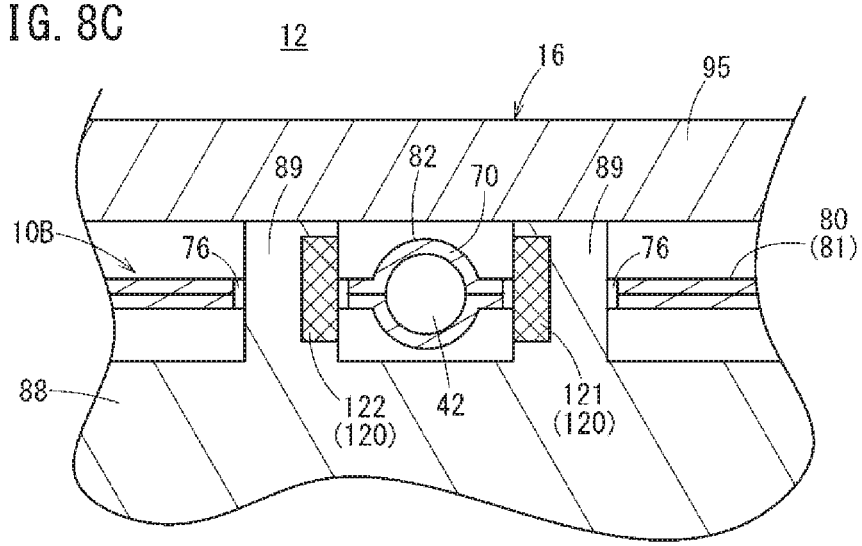
FIG. 8C is a cross-sectional view of a principal part of the blood component collection cassette of FIG. 8A.

Further, a cassette 10B according to another modification, as shown in FIGS. 8A to 8C, includes the first constituent part 80 and the second constituent part 82 in the same manner as the cassette 10, but differs from the cassettes 10, 10A in that holes 76 are provided in the cassette main body 40 at positions in close proximity to the second constituent part 82.

A pair of holes 76 are provided that sandwich the second constituent part 82 therebetween, and a pair of protrusions 89, in which detection units 120 are provided, are inserted respectively into the holes 76 upon being mounted in the cassette mounting unit 88. The pair of holes 76 are formed with rectangular shapes as viewed in plan, and the length in the longitudinal direction thereof coincides substantially with the length over which the second constituent part 82 extends. Further, since the protrusions 89 are formed with the same shape, and are slightly smaller than the holes 76 as viewed in plan, the protrusions 89 can be easily inserted into the holes 76.

For example, for the detection units 120, optical sensors can be applied, and the detection units 120 include a transmission unit 121 and a reception unit 122, which are disposed to face each other, with (the flow path 42 of) the second constituent part 82 being interposed therebetween. In addition, the detection units 120 output measurement waves (ultrasonic waves, measurement light) from the transmission unit 121 to the second constituent part 82, and the reception unit 122 receives the transmitted waves which are transmitted through the flow path 42. As noted above, since the outer surface of the second constituent part 82 is not provided with the concavities and convexities, it is possible to suitably suppress attenuation of the measurement waves and the transmitted waves. Accordingly, similar to the case of the cassette 10, with the cassette 10B as well, the blood component collection system 12 is capable of accurately detecting the state of the liquid flowing through the flow path 42.

Further, since the holes 76 are disposed in the vicinity of the second constituent part 82, the lid 95 of the centrifugal separation device 16 can be made with a simple structure. Furthermore, the holes 76 facilitate positioning of the cassette 10B with respect to the cassette mounting unit 88, and it is possible to enhance fixation thereof when the cassette 10B is mounted.

It is a matter of course that the blood component collection cassettes 10, 10A and 10B according to the present invention are not limited to being applied to the blood component collection system 12. The blood component collection cassettes (biological component collection cassettes) 10, 10A and 10B can be applied to various systems through which a liquid is made to flow through the flow path 42, for example, a whole blood donation system, a culture apparatus for various types of cells which are collected or cultured from patients or donors, or alternatively, a medicinal solution administration system.

The invention claimed is:

1. A biological component collection cassette having a flow path through which a liquid containing at least one biological component flows, comprising:
   a cassette main body including a first flexible sheet and a second flexible sheet,
   wherein the cassette main body includes an outer surface having a first part that includes a plurality of concavities and convexities, and a second part on which the plurality of concavities and convexities do not exist,
   wherein the second part is provided:
      on at least a first portion of a flow path wall of the flow path; and
      on the outer surface of the cassette main body along a border of the flow path that corresponds to a sealed section between the first flexible sheet and the second flexible sheet, and
   wherein the first part is provided:
      on at least a second portion of the flow path wall; and
      on a section of the outer surface of the cassette main body that is adjacent to the sealed section.

2. The biological component collection cassette according to claim 1, wherein the second part has a transmittance higher than a transmittance of the first part.

3. The biological component collection cassette according to claim 2, wherein the plurality of concavities and convexities correspond to embossments.

4. The biological component collection cassette according to claim 2, wherein the second part is provided on a region for detecting the presence of fluid in the flow path.

5. The biological component collection cassette according to claim 1, wherein the second part has a length that is 10% or less than a total length of the flow path.

6. The biological component collection cassette according to claim 1, wherein the first part has an area which is greater than or equal to 80% of an area of the outer surface of the cassette main body.

7. The biological component collection cassette according to claim 1, wherein the second part is disposed on an outer surface on the first flexible sheet and an outer surface of the second flexible sheet.

8. The biological component collection cassette according to claim 1, wherein:
   the flow path includes a plurality of branching paths, and a trunk path that communicates with the plurality of branching paths, and
   the second part is located in the trunk path.

9. The biological component collection cassette according to claim 1, wherein first and second flexible sheets are made from any one of a vinyl chloride resin, a polyolefin resin, and a polyurethane resin.

10. The biological component collection cassette according to claim 1, wherein the first and second flexible sheets are bonded to each other at the sealed section to form said flow path.

11. The biological component collection cassette according to claim 1, wherein the second part is provided along an entire border of the flow path.

12. The biological component collection cassette according to claim 1, wherein the sealed section is recessed from the section of the outer surface of the cassette main body that is adjacent to the sealed section.

13. The biological component collection cassette according to claim 1, wherein inner surfaces of said first and second flexible sheets are smooth.

14. The biological component collection cassette according to claim 1, wherein the first portion of the flow path wall is closer to a first edge of the cassette main body opposite a second edge of the cassette main body.

15. The biological component collection cassette according to claim 14, wherein the first portion of the flow path wall is between the first edge of the cassette main body and a branch in the flow path.

16. The biological component collection cassette according to claim 1, wherein the second part is provided on a region for detecting the presence of fluid in the flow path.

17. The biological component collection cassette according to claim 1, wherein the second portion of the flow path wall comprises a first region and a second region each having the plurality of concavities and convexities, and wherein the first portion of the flow path wall is between the first region and the second region.

18. A biological component collection system comprising:
   a biological component collection kit including a tube;
   a biological component collection cassette communicating with the tube, and having a flow path through which a liquid containing at least one biological component flows;
   a biological component separation device to which the biological component collection kit is attached, and through which the at least one biological component contained within the liquid is allowed to flow;
   wherein the biological component collection cassette comprises a cassette main body including a first flexible sheet and a second flexible sheet,
   wherein the cassette main body includes an outer surface having a first part that includes a plurality of concavities and convexities, and a second part on which the plurality of concavities and convexities do not exist,
   wherein the second part is provided:
      on at least a first portion of a flow path wall of the flow path; and
      on the outer surface of the cassette main body along a border of the flow path that corresponds to a sealed section between the first flexible sheet and the second flexible sheet, wherein the first part is provided:
  on at least a second portion of the flow path wall; and
  on a section the outer surface of the cassette main body that is adjacent to the sealed section,
wherein the biological component separation device includes a cassette mount in which the biological component collection cassette is mounted, and
wherein the cassette mount includes a sensor to detect a state of the liquid, the sensor facing toward the second part.

19. The biological component collection system according to claim 18, wherein the second part has a transmittance higher than a transmittance of the first part.

20. A method of manufacturing a biological component collection cassette having a flow path through which a liquid containing at least one biological component flows, the method comprising:
  forming a first part on an outer surface of first and second resin sheets, the first part having a plurality of concavities and convexities;
  forming a second part on the outer surface of the first and second resin sheets by applying heat to a predetermined position of the first and second resin sheets to make the second part smooth; and
  sealing the first and second resin sheets along a sealed section to form a flow path wall of the flow path, the flow path wall comprising the first part and the second part, wherein sealing the first and second resin sheets makes the plurality of concavities and convexities smooth along a border of the flow path that corresponds to the sealed section between the first resin sheet and the second resin sheet.

* * * * *